United States Patent [19]

Haberkorn et al.

[11] 4,219,552

[45] Aug. 26, 1980

[54] 1-(4-PHENOXY-PHENYL)-1,3,5-TRIAZINES, THEIR USE AS GROWTH PROMOTERS

[75] Inventors: Axel Haberkorn; Martin Scheer, both of Wuppertal; Jürgen Stoltefuss, Haan, all of Fed. Rep. of Germany

[73] Assignee: Bayer Atkiengesellschaft, Leverkusen, Fed. Rep. of Germany

[21] Appl. No.: 19,549

[22] Filed: Mar. 12, 1979

Related U.S. Application Data

[63] Continuation of Ser. No. 843,627, Oct. 19, 1977, abandoned.

[30] Foreign Application Priority Data

Apr. 27, 1977 [DE] Fed. Rep. of Germany ....... 2718799

[51] Int. Cl.² .................. C07D 251/34; A61K 31/53
[52] U.S. Cl. .................................... 424/249; 544/221
[58] Field of Search ......................... 544/221; 424/249

[56] References Cited

U.S. PATENT DOCUMENTS

| | | | |
|---|---|---|---|
| 3,933,814 | 1/1976 | Haberkorn et al. | 544/221 |
| 3,948,893 | 4/1976 | Aichinger et al. | 544/221 |
| 3,966,725 | 6/1976 | Reisdorff et al. | 544/221 |

*Primary Examiner*—John M. Ford
*Attorney, Agent, or Firm*—Sprung, Felfe, Horn, Lynch & Kramer

[57] ABSTRACT

The invention relates to new (4-phenoxy-phenyl)-1,3,5-triazine derivatives of the formula

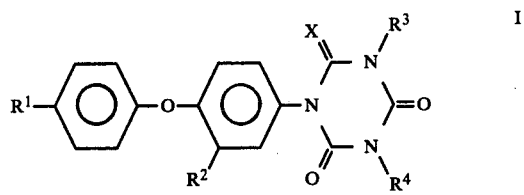

in which
  $R^1$ represents halogenoalkylthio, halogenalkylsulphinyl or halogenoalkylsulphonyl,
  $R^2$ represents hydrogen, alkyl, alkoxy, alkoxyalkyl, alkylmercapto, halogen, halogenalkyl or an optionally substituted sulphamoyl, such as dialkyl, sulphamoyl, radical,
  $R^3$ and $R^4$ can be identical or different and represent hydrogen, alkyl, alkenyl or alkinyl and
  X is O or S, and their physiologically acceptable salts. The compounds have a very good coccidiostatic action and an excellent growth promoting action.

Also included in the invention are compositions containing said compounds and methods for their preparation and use.

3 Claims, No Drawings

1-(4-PHENOXY-PHENYL)-1,3,5-TRIAZINES, THEIR USE AS GROWTH PROMOTERS

This is a continuation of application Ser. No. 843,627 filed Oct. 19, 1977, now abandoned.

The present invention relates to new 1-(4-phenoxy-phenyl)-1,3,5-triazine derivatives, several processes for their preparation and their use as medicaments and growth promotors.

An action as a medicament is, in particular, the action as a coccidiostatic agent.

It has now been found that the new 1-(4-phenoxy-phenyl)-1,3,5-triazine derivatives of the formula

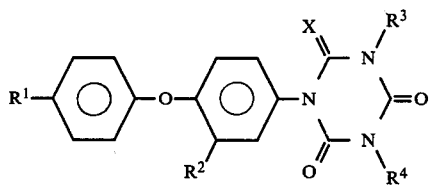

in which $R^1$ represents halogenoalkylthio, halogenoalkyl-sulphinyl or halogenoalkylsulphonyl, $R^2$ represents hydrogen, alkyl, alkoxy, alkoxyalkyl, alkylmercapto, halogen, halogenoalkyl or an optionally substituted sulphamoyl, such as dialkyl sulphamoyl, radical, $R^3$ and $R^4$ can be identical or different and represent hydrogen, alkyl, alkenyl or alkinyl and X is O or S, and their physiologically acceptable salts have a very good coccidiostatic action and an excellent growth promotion action.

Furthermore, it as been found that, in particular, the following compounds of the formula Ia and their physiologically acceptable salts have, in addition to a coccidiostatic action, an excellent growth promotor action:

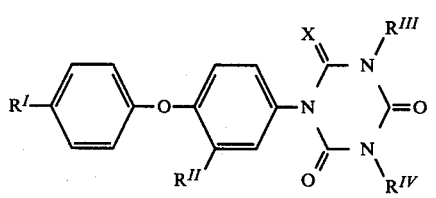

in which $R^I$ represents halogenoalkyl($C_1$-$C_4$)-thio, halogenoalkyl($C_1$-$C_4$)-sulphinyl or halogenoalkyl($C_1$-$C_4$)-sulphonyl, $R^{II}$ represents hydrogen, alkyl ($C_1$-$C_4$), alkoxy ($C_1$-$C_4$), halogen, alkoxy($C_1$-$C_4$)alkyl($C_1$-$C_4$), alkyl ($C_1$-$C_4$)- mercapto, dialkyl ($C_1$-$C_4$)aminosulphonyl or halogenoalkyl ($C_1$-$C_4$) and $R^{III}$ and $R^{IV}$ can be identical or different and represent hydrogen, alkyl ($C_1$-$C_4$) or alkenyl ($C_2$-$C_4$) and X is O or S. and X is O or S. Finally, it has been found that (a) 1-(4-phenoxy-phenyl)-1,3,5-triazines of the formula I are obtained when compounds of the formula II

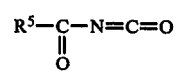

in which $R^1$, $R^2$, $R^3$ and X have the meaning indicated above, are reacted with a substituted carbonyl isocyanate of the formula III $$R^5-\underset{\underset{O}{\|}}{C}-N=C=O \qquad III$$

in which $R^5$ represents a halogen atom, an alkoxy group or an aryloxy group, and the substituted 1,3,5-triazine derivatives, formed during this procedure, of the formula IV

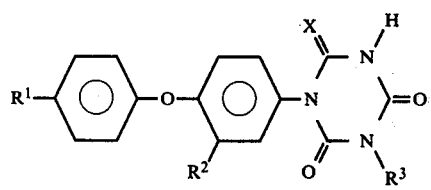

in which $R^1$, $R^2$, $R^3$ and X have the meaning indicated above, are optionally isolated and optionally reacted with a compound of the formula V $$A-Z \qquad V$$

wherein

A represents alkyl, alkenyl or alkinyl and

Z represents halogen;

or that (b) 1-(4-phenoxy-phenyl)-1,3-triazine derivatives of the general formula I are obtained when compounds of the the formula II, in which $R^1$, $R^2$, $R^3$ and X have the meaning indicated above, are reacted with bis-(chlorocarbonyl)-amines of the formula VI

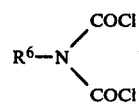

in which $R^6$ represents alkyl, optionally in the presence of acid acceptors, or that (c) in order to obtain compounds of the formula I in which the substituents $R^2$, $R^3$ and $R^4$ as well as X have the meaning indicated above and $R^1$ represents halogenoalkylsulphinyl or halogenoalkylsulphonyl, compounds of the formula

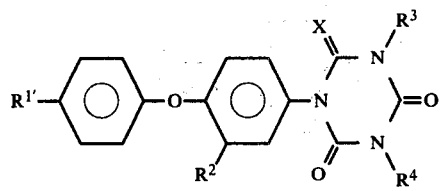

VII in which
$R^2$, $R^3$ and $R^4$ have the meaning indicated above and
$R^{1'}$ represents halogenoalkylthio,
are reacted with the appropriate amount of a suitable oxidising agent.

Surprisingly, the 1-(4-phenoxy-phenyl)-1,3,5-triazines according to the invention exhibit an excellent growth promoter action, in addition to an action against coccidiosis in poultry and mammals. With regard to the practical use, the combination of this type of action is extremely useful, especially since the commerically available substances known according to the state of the art, such as 3,5-dinitrotoluyl-amide, 1-[(4-amino-2-propyl-5-pyrimidinyl))-methyl]-2-picolinium chloride hydrochloride, 3,5-dichloro-2,6-dimethyl-4-pyridone and the complex of 4,4'-di-(nitrophenyl)-urea, 4,6-dimethyl-2-hydroxy-pyrimidine, Monensin and Lasalocid, do not exhibit this type of effect.

In addition, they are also distinguished by the fact that they have an action both against coccidiosis in poultry and against coccidiosis in mammals. This breadth of action is not known in the commercially available coccidiosis agents.

If N-[3-chloro-4-(4'-trifluoromethylthio-phenoxy)-phenyl]-N'-methyl-urea and chlorocarbonyl isocyanate are used in process variant (a), the course of the reaction can be represented by the following equation:

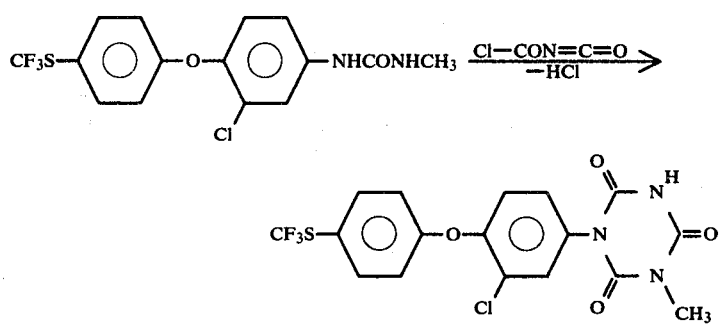

If N-[3-ethoxy-4-(4'-trifluoromethylthio-phenoxy)-phenyl]-thiourea and N-methyl-bis-(chlorocarbonyl)-amine are used as the starting materials in process variant (b), the course of the reaction can be represented by the following equation:

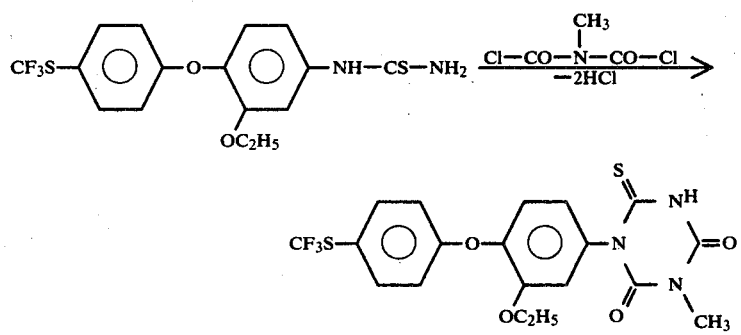

The compounds of the general formula I, obtained according to process variant (a) or (b), in which $R_1$ = halogenoalkylthio and $X=0$ can be oxidised according to process varient (c) to the corresponding halogenoalkylsulphinyl or halogenoalkylsulphonyl derivatives. If hydrogen peroxide is used as the oxidising agent, the course of the reaction can be represented by the following equation:

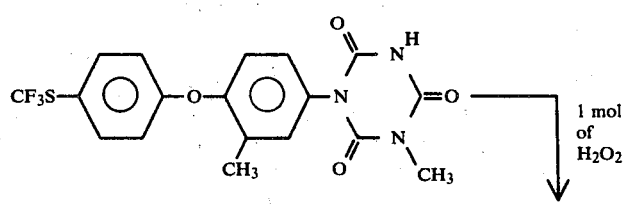

-continued

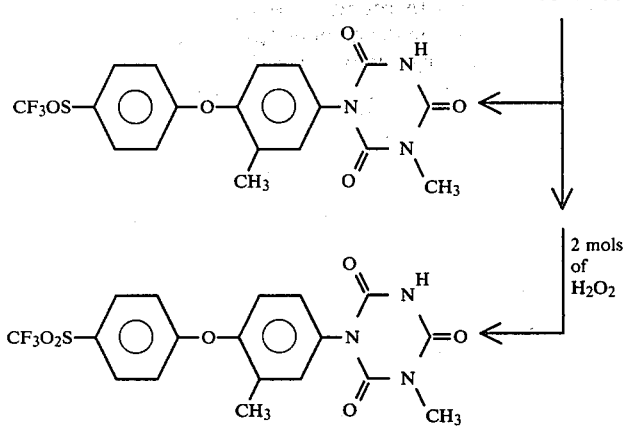

In the formulae I, II, IV, V, VI and VII, alkyl as defined in $R^2$, $R^3$, $R^4$, $R^6$ or A is straight-chain or branched alkyl with preferably 1 to 6, in particular 1 to 4, carbon atoms. Examples which may be mentioned are optionally substituted methyl, ethyl, n- and i-propyl and n-, i- and t-butyl.

In the formulae I, II, IV, V and VII, alkenyl as defined in $R^3$, $R^4$ or A is straight-chain or branched alkenyl with preferably 2 to 6, in particular 2 to 4, carbon atoms. Examples which may be mentioned are optionally substituted ethenyl, propen-1-yl, propen-2-yl and buten-3-yl.

In the formulae I, II, IV, V and VII, alkinyl as defined in $R^3$, $R^4$ or A is straight-chain or branched alkinyl with preferably 2 to 6, in particular 2 to 4, carbon atoms. Examples which may be mentioned are optionally substituted ethinyl, propen-1-yl, propin-2-yl and butin-3-yl.

In the formulae I, II, III, IV and VII, alkoxy as defined in $R^2$ or $R^5$ is straight-chain or branched alkoxy with preferably 1 to 6, in particular 1 to 4, carbon atoms. Examples which may be mentioned are optionally substituted methoxy, ethoxy, n- and i-propoxy and n- and i-butoxy.

In the formulae I, II, III, IV, V and VII, halogen as defined in $R^2$, $R^5$ or Z is preferably fluorine, chlorine, bromine and iodine, especially chlorine and bromine.

In the formulae I, II, IV and VII, halogenoalkylthio as defined in $R^1$ is halogenoalkylthio with preferably 1 to 4, in particular 1 or 2, carbon atoms preferably 1 to 5, in particular 1 to 3, identical or different halogen atoms, halogen atoms preferably being fluorine, chlorine and bromine, especially fluorine and chlorine. Examples which may be mentioned are trifluoromethylthio, chloro-di-fluoromethylthio, bromomethylthio, 2,2,2-trifluoroethylthio and pentafluoroethylthio.

In the formulae I, II and IV, halogenoalkylsulphinyl as defined in $R^1$ is halogenoalkylsulphinyl with preferably 1 to 4, in particular 1 or 2, carbon atoms and preferably 1 to 5, in particular 1 to 3, identical or different halogen atoms, halogen atoms preferably being fluorine, chlorine and bromine, especially fluorine and chlorine. Examples which may be mentioned are trifluoromethylsulphuryl, chloro-di-fluoromethylsulphuryl, bromomethylsulphinyl, 2,2,2-trifluoroethylsulphinyl and pentafluoroethylsulphinyl.

In the formulae I, II and IV, halogenoalkylsulphonyl as defined in $R^1$ is halogenoalklysulphonyl with preferably 1 to 4, in particular 1 or 2, carbon atoms and preferably 1 to 5, in particular 1 to 3, identical or different halogen atoms, halogen atoms preferably being fluorine, chlorine and bromine, especially fluorine and chlorine. Examples which may be mentioned are trifluoromethylsulphonyl, chloro-di-fluoromethylsulphonyl, bromomethylsulphonyl, 2,2,2-trifluoroethylsulphonyl and pentafluoroethylsulphonyl.

In the formulae I, II, and IV, optionally substituted sulphamoyl as defined in $R^2$ is preferably one of the following radicals:

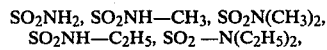

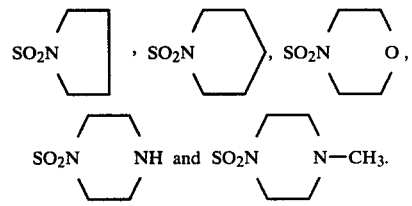

In the formulae III, aryloxy as defined in $R^5$ is preferably monocyclic carbocyclic aryloxy or bicyclic carbocyclic aryloxy, particularly phenoxy.

In the formulae III, aryloxy $R^5$ is preferably phenoxy.

Most of the substituted ureas or thioureas of the formula II which are used as starting materials have not been known hitherto, but they can be easily prepared by methods which are in themselves known by (a) either reacting substituted 4-aminodiphenyl ethers with the corresponding substituted isocyanates or isothiocyanates in an inert solvent at temperatures between 0° C. and 100° C., or, reversing the sequence, (b) reacting ammonia or substituted amines and the corresponding substituted 4-isocyanato or 4-isothiocyanato-diphenyl ethers with one another under the same conditions, or by (c) subjecting substituted 4-hydroxyphenyl-ureas or -thioureas to a condensation reaction with activated halogenoaromatic compounds in aprotic solvents, such as dimethylsulphoxide, dimethylform-amide or hexamethylphosphoric acid triamide, in the presence of bases, such as sodium hydride, potassium hydroxide, potassium carbonate z.a.m., at temperatures between 20° C. and 150° C.

When the amount of solvent is appropriately chosen, the reaction products generally crystallise out on cooling the solution. Literature for the alternate preparation of ureas from amines and isocyanates is: Methoden der Org. Chemie (Methods of Organic Chemistry) (Houben-Weyl), IVth edition, Volume VIII, page 157-158.

Some of the bis-(chlorocarbonyl)-amines of the general formula VI which can be used according to the invention in process (b) are already known (compare the article in Synthesis 1970, page 542-543) and, if they are not yet known, they can be prepared in an analogous manner from cyclic diacyldisulphides and chlorination in inert organic solvents, preferably in carbon tetrachloride.

Possible diluents for the reaction of the ureas or thioureas of the formula II both with carbonyl isocyanates of the formula III (process variant a) and with bis-(chlorocarbonyl)-amines of the formula VI (process variant b) as well as for the reaction of the 1,3,5-triazine derivatives of the formula IV with compounds of the formula A-Z are all the organic solvents which are inert in these reactions.

These include, in addition to the pyridine, preferably, aromatic hydrocarbons, such as benzene, toluene and xylene, halogenated aromatic hydrocarbons, such as chlorobenzene and dichlorobenzene, and ethers, such as tetrahydrofurane and dioxane.

The hydrochloric acid which may form during the reaction escapes as a gas or can be bonded by organic or inorganic acid acceptors. The acid acceptors include, preferably, tertiary organic bases, such as trialkylamines, for example, triethylamine, N-hetero mono- or bi-cyclic aromatic amines, such as pyridine aza-cyclo alkyl amines which are mono- or bi- cyclic, such as diazabicyclononene, diazabicycloundecene and many others, or inorganic bases, such as alkali metal carbonates, oxides or hydroxides or alkaline earth metal carbonates, oxides or hydroxides.

The reaction temperatures for the above-mentioned reaction stages can be varied within a wide range. In general, the reaction is carried out between about 0° C. and about 150° C., preferably between about 20° C. and about 100° C.

In the above-mentioned reaction stages, the reaction can be carried out under normal pressure or under elevated pressure. In general, the reaction is carried out under normal pressure.

Possible oxidising agents for the conversion, according to process variant (c) of the trifluoromethylthio compounds of the general formula I, in which Y represents oxygen, into the corresponding sulphinyl or sulphonyl compounds are, appropriately: $H_2O_2$/glacial acetic acid; $H_2O_2$/acetic anhydride; $H_2O_2$/methanol; peracids, such as, for example, m-chloroperbenzoic acid, and chromic acid; potassium permanganate; sodium periodate, ceric ammonium nitrate; and nitric acid.

A resulting compound can be converted into a corresponding addition salt, for example by reacting it with an inorganic or organic base.

The new active compounds, and their salts, exhibit a marked growth promotor action, that is to say they promote weight development in, for example, chickens, rabbits and pigs, with a simultaneously reduced feed consumption, compared with untreated controls. A considerable improvement in the feed utilisation is thereby achieved.

The feeding experiments were carred out in the following manner:

3 day old hybrids (broilers) sorted according to sex were used. 20 animals were employed for formulation and dose.

Pure chick feed, without the addition of antibiotics, commercially available coccidiostatic agents and stabilising auxiliaries, was given to animals kept in cages. The substances to be tested were intermixed with this feed. Feed and water were available ad libitum. The temperature was 28° C. at the start of the experiment and about 23° C. at the end. of the experiment.

The animals were exposed to synthetic light 16 hours per day. At the start of the experiment, all the animals of one experimental group had the same starting weight. The duration of the experiment was over 14 days.

The weight increase rates and the feed consumption were used as evaluation criteria.

Administering the new active compounds as a feedstuff additive leads to accelerated growth, accelerated weight increase and better feed utilisation. The active compounds can be admixed to any desired feed and/or to the drinking water in the customary manner and thus be administered to the animals. They can, of course, also be admixed to feed concentrates and to formulations containing vitamins and/or mineral substances. The compounds obtainable according to the invention are preferably added to the feed, to feed formulations or to the drinking water in amounts of about 1 to about 200 ppm, in particular 10 to 50 ppm. However, it can be appropriate to increase or to reduce the concentration of the active compound, depending on the species of animal, the age of the animals and the general conditions of keeping the animals. Particularly good successes in promoting the growth and in the feed utilisation are achieved in the rearing of young animals, such as, for example, calves and piglets, as well as poultry, such as, for example, chicks.

The good properties as a feedstuff additive can be seen from the feed experiments which follow (Table 1).

The experimental animals used were chicks which were kept in cages and which had feed (complete chick feed) and water available ad libitum.

The active compounds were mixed, in the finely divided form, into the feed using a mixing machine. The experiments were repeated several times and the duration of the experiment was 14 days.

Table 1

Weight development in chicks (average values of several experiments) after feeding with the active compound

| Active compound | Number of the animals | experiments | Active compound concentration in the feed in ppm | Weight development in per cent | Feed consumption in per cent |
|---|---|---|---|---|---|
| untreated control | 135 | 3 | — | 100 | 100 |
| compound from Example 2 | 68 | 3 | 25 | 102.6 | 96.2 |
|  | 68 | 3 | 50 | 100.5 | 93.3 |
| compound from Example 1 | 48 | 2 | 25 | 109.9 | 95.4 |
|  | 48 | 2 | 50 | 109.2 | 97.1 |

The new active compounds, and their salts, exhibit powerful coccidiocidal actions. They are highly active against the species of Coccidia in poultry, such as, for example, Eimeria tenella (coccidiosis of the appendix in hens), E. acervulina, E. brunetti, E. maxima, E. mitis, E. mivati, E. necatrix and E. praecox (coccidiosis of the small intestine/hen). The formulations can also be employed for the prophylaxis and treatment of coccidiosis infections of other species of domestic poultry. The new active compounds are, in addition, also distinguished by a very powerful action on coccidial infections in mammals, such as, for example, in rabbits (E. stiedae/coccidiosis of the liver, E. magna, E. media, E. irresidua and E. perforans/coccidiosis of the intestine), in sheep, cattle and other domestic animals, including dogs and cats, as well as in laboratory animals, such as white mice (E. falciformis) and rats.

The new active compounds can be converted in a known manner into the customary formulations, such as premixes for administration with the feed, tablets, dragées, capsules, suspensions and syrups.

The compounds for combating coccidiosis are indeed usually most appropriately administered in or with the feed or in the drinking water; however, the compounds can also be administered to individual animals in the form of tablets, medicinal drinks, capsules or the like or by injection or by pouring on.

Using the compounds according to the invention, a feed containing the active compound is usually prepared by thoroughly mixing about 5–5,000, preferably about 5–250, ppm of active compound with a nutritionally balanced animal feed, for example with the chick feed described in the example which follows.

The following composition is an example of the use of the substances according to the invention in poultry feed:

---
52.0000% shredded cereal feed
17.9975% of shredded soya
5.0000% of maize gluten feed
5.0000% of wheat wholemeal
3.0000% of fishmeal
3.0000% of tapioca meal
3.0000% of green lucerne meal
2.0000% of wheatgerm, comminuted
2.0000% of soya oil
1.6000% of fishbone meal
1.5000% of whey powder
1.4000% of carbonated feed lime
1.0000% of feed lime phosphate
1.0000% of molasses
0.5000% of brewer's yeast
0.0025% of 1-[3-chloro-4-(4'-trifluoromethylthio-phenoxy)-phenyl]-3-methyl-1,3,5-triazine-2,4,6(1H,3H,5H)-trione
100.0000%
---

Such a feed is suitable both for curative and for prophylactic use.

PREPARATION EXAMPLE 1

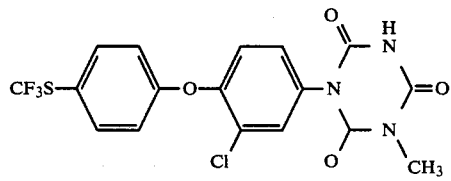

2.64 g (7 mmols) of N-[3-chloro-4-(4'-trifluoromethyl-thio-phenoxy)-phenyl]-N'-methyl-urea of melting point 146° are suspended in 12.9 ml of absolute toluene, and a solution of 0.92 g (8.6 mmols) of chlorocarbonyl isocyanate in 1 ml of absolute toluene is added dropwise, whilst stirring. The mixture is stirred for 30 minutes at room temperature and the clear solution is heated to the boil for 2 hours. It is cooled to 10° C. and the resulting crystals are filtered off, washed with toluene and petroleum ether and dried at 100° in vacuo. This gives 2.76 g (89% of theory) of 1-[3-chloro-4-(4'-trifluoromethylthio-phenoxy)-phenyl]-3-methyl-1,3,5-triazine-2,4,6(1H, 3H, 5H)-trione of melting point 186° C.

The following compounds are obtained analogously and can be substituted for the active compounds shown in the feed experiments shown above: Example No.
2   1-[3-Methyl-4-(4'-trifluoromethylthio-phenoxy)-phenyl]-3-methyl-1,3,5-triazine-2,4,6(1H,3H,5H)-trione, melting point: 194° C.
3   1-[3-Methyl-4-(4'-trifluoromethylsulphonyl-phenoxy)-phenyl ]-3-methyl-1,3,5-triazine-2,4,6(1H,3H,5H)-trione, melting point: 242° C.
4   1-[3-Methoxy-4-(4'-trifluoromethylthio-phenoxy)-phenyl]-3-methyl-1,3,5-triazine-2,4,6(1H,3H,5H)-trione, melting point: 216° C.
5   1-[3-Chloro-4-(4'-trifluoromethylsulphonyl-phenoxy)-phenyl[-3-methyl-1,3,5-triazine-2,4,6(1H,3H,5H)-trione, melting point: 260° C.
6   1-[3-Methoxy-4-(4'-trifluoromethylsulphonyl-phenoxy)-phenyl]-3-methyl-1,3,5-triazine-2,4,6(1H,3H,5H)-trione, melting point: 255° C.
7   1-[3-Ethoxy-4-(4'-trifluoromethylsulphonyl-phenoxy)-phenyl]-3-methyl-1,3,5-triazine-2,4,6(1H,3H, 5H)-trione, melting point: 247° C.
8   1-[3-Ethoxy-4-(4'-trifluoromethylthio-phenoxy)-phenyl]-3-methyl-1,3,5-triazine-2,4,6(1H,3H,5H)-trione, melting point: 227° C.
9   1-[3-Dimethylaminosulphonyl-4-(4'-trifluoromethylsulphonyl-phenoxy)-phenyl]-3-methyl-1,3,5-triazine-2,4,6(1H,3H,5H)-trione, melting point: >300° C.
10  1-[3-Dimethylaminosulphonyl-4-(4'-trifluoromethylthiophenoxy)-phenyl]-3-methyl-1,3,5-triazine-2,4,6(1H,3H,5H)- trione, melting point: >300° C.
11  1-[3-Trifluoromethyl-4-(4'-trifluoromethylthio-phenoxy)-phenyl]-3-methyl-1,3,5,    -triazine-2,4,6(1H,3H,5H)-trione, melting point: 170° C.

EXAMPLE 12

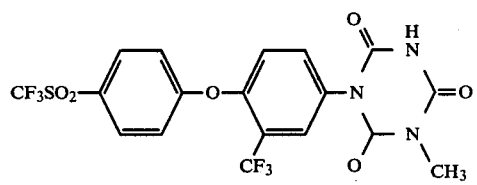

5.2 g (45 mmols) of 30% strength hydrogen peroxide are added dropwise, at 20°, to a solution of 4.79 g (10 mmols) of 1-[3-trifluoromethyl-4-(4'-trifluoromethylthio-phenoxy)-phenyl]-3-methyl-1,3,5-triazine-2,4,6(1H,3H,5H)-trione, of melting point: 170° C., in 30 ml of anhydrous acetic acid. The mixture is heated to the boil for 2 hours, whilst stirring, 3 ml of water are added and the mixture is cooled, whilst stirring. The crystals which have precipitated are filtered off and washed with 50% strength acetic acid and then with water. This gives 4.1 g (82.5% of theory) of 1-[3-tri-fluoromethyl-4-(4'-trifluoromethyl-sulphonyl-phenoxy)-phenyl]-3methyl-1,3,5-triazine-2,4,6(1H,3H,5H)-trione of melting point: 238° C.

The following was prepared analogously

EXAMPLE 13

1-[3-Morpholinosulphonyl-4-(4'-trifluoromethyl-sulphonylphenoxy)-phenyl]-3-methyl-1,3,5-triazine-2,4,6(1H,3H,5H)-trione, melting point: 309° C.

EXAMPLE 14

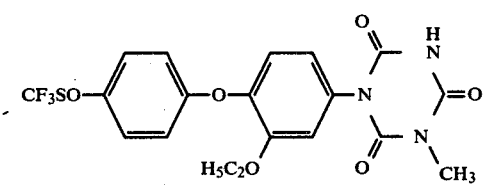

0.94 g. (11 mmols) of 30% strength hydrogen peroxide is added to a solution of 4.55 g (10 mmols) of 1-[3-ethoxy-4 -(4'-trifluoromethylthio-phenoxy)-phenyl]-3-methyl-1,3,5-triazine-2,4,6(1H,3H,5H)-trione of melting point: 227° C. in 140 ml of anhydrous acetic acid. The mixture is stirred for 3 days at 50° C. and 140 ml of water are then added dropwise. The crystals which have precipitated are filtered off and recrystallised from isopropanol. This gives 2.4 g (51% of theory) of 1-[3-ethoxy-4-(4'-trifluoromethylsulphinyl-phenoxy)-phenyl]- 3-methyl- 1,3,5-triazine-2,4,6(1H,3H,5H)-trione of melting point: 225° C.

The following was obtained in an analogous manner:

EXAMPLE 15

1-[3-Methyl-4-(4'-trifluoromethylsulphinyl-phenoxy)-phenyl]-3-methyl-1,3,5-triazine-2,4,6(1H,3H,5H)-trione, melting point: 130° C.

What is claimed is:

1. A medicament, characterized in that it contains a growth-promoting effective amount of at least one 1-(4-phenoxy-phenyl)-1,3,5-triazine of the formula

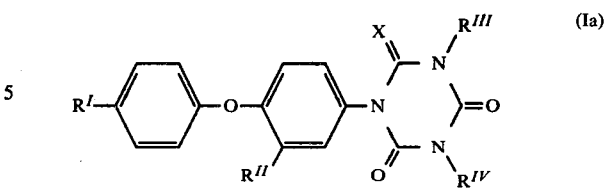

in which $R^I$ represents perfluoroalkyl ($C_1$–$C_4$) thio, halogenoalkyl ($C_{1-C4}$) sulphinyl or halogenoalkyl ($C_{1-C4}$) sulphonyl, $R^{II}$ represents alkyl ($C_1$–$C_4$) or halogen, and $R^{III}$ and $R^{IV}$ are identical or different and represent hydrogen or alkyl ($C_1$–$C_4$), X represents an oxygen atom or a sulphur atom, and its physiologically acceptable salts.

2. A growth promoting agent, characterized in that it contains a growth-promoting effective amount of at least one 1-(4-phenoxy-phenyl)-1,3,5-triazine according to claim 1.

3. Process for promoting growth in animals, characterized in that a growth-promoting effective amount of a 1-(4-phenoxy-phenyl)-1, 3, 5-triazine of the formula

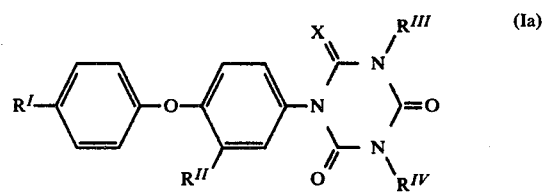

in which $R^I$ represents perfluoroalkyl ($C_{1^--C4}$) thio, halogenoalkyl ($C_1$–$C_4$) sulphinyl or halogenoalkyl ($C_1$–$C_4$) sulphonyl, $R^{II}$ represents alkyl ($C_1$–$C_4$) or halogen, and $R^{III}$ and $R^{IV}$ are identical or different and represent hydrogen or alkyl ($C_1$–$C_4$), X represents an oxygen atom or sulphur atom, and its physiologically acceptable salts is administered to animals.

* * * * *